United States Patent [19]

Jacobstein

[11] Patent Number: 4,512,601
[45] Date of Patent: Apr. 23, 1985

[54] CONTACT LENS HANDLING DEVICE

[75] Inventor: Benjamin Jacobstein, Coral Gables, Fla.

[73] Assignee: Scientific Technology, Ltd., Coral Gables, Fla.

[21] Appl. No.: 526,332

[22] Filed: Aug. 25, 1983

[51] Int. Cl.³ .............................................. A61F 9/00
[52] U.S. Cl. ........................................ 294/1.2; 294/25
[58] Field of Search ................... 294/1 R, 1 CA, 25; 2/21; 206/5.1, 447, 460

[56] References Cited

U.S. PATENT DOCUMENTS

| | | | |
|---|---|---|---|
| 3,132,887 | 5/1964 | Martinez | 294/1 CA X |
| 3,283,888 | 11/1966 | Scott | 294/25 X |
| 3,411,364 | 11/1968 | Horley et al. | 294/1 CA X |
| 3,584,908 | 6/1971 | Ray | 294/1 CA |
| 3,972,325 | 8/1976 | Bluestone | 2/21 X |
| 3,985,383 | 10/1976 | Yonkers | 294/25 |

*Primary Examiner*—Johnny D. Cherry
*Attorney, Agent, or Firm*—Wegner & Bretschneider

[57] ABSTRACT

A device is disclosed for aiding in the handling of contact lenses which is generally placed on the fingertip and includes a disc coated on at least one side with an adhesive layer and a central aperture. The disc is composed of bio-compatible material and includes on at least one surface either a layer of bio-compatible adhesive or an adhesive coated band attached to the disc. The adhesive provides a firm attachment to the fingertip or other surfaces and the central aperture supports the contact lens to maintain its shape for transfer to the correspondingly shaped surface of the eye.

14 Claims, 7 Drawing Figures

CONTACT LENS HANDLING DEVICE

BACKGROUND OF THE INVENTION

1. Field of the Invention

The present invention relates to an improved device for the handling of contact lenses, and more particularly, to a device for the insertion of soft contact lenses.

2. Description of the Prior Art

Applicators and devices for the handling of both soft and hard contact lenses are known in the art. The development of these devices has followed the evolution of the contact lens itself, with the early applicators designed for use with rigid contact lenses and subsequent devices designed to accommodate hydrophylic or soft contact lenses. Although the need for an effective way of handling these lenses remains, the need for a handling device which is simple enough for patient use has become acute with the development and increasing popularity of the ultra thin contact lenses, such as "extended wear" lenses.

The prior art devices range in complexity from elaborate apparatuses with suction means for holding the lens and various handles for manipulation of the lens during application or removal (U.S. Pat. Nos. 2,384,334 and 2,919,696) to less intricate devices which rely on surface tension to hold the contact lens on the manipulating means which is attached to a handle portion for applying and removing the lens (U.S. Pat. No. 4,088,359). Such devices have not gained wide acceptance by contact lens users because they are relatively complex, inconvenient, and difficult to use when compared with the handling means of choice, namely, simple use of the finger tips. Although the finger tips are a convenient means for handling contact lenses, their use is not appropriate in many situations. For example, when attempting to handle the ultra thin "extended wear" lenses the flat or convex shape of the fingertip results in the collapse of the contact lens on the surface of the fingertip. This results in increased adhesion of the lens to the fingertip and difficulty in the transfer to the surface of the eye.

During the removal of contact lenses from the eye the generally accepted concurrent use of the user's index finger and thumb to extract either soft or hard lenses from the eye involve the risk of both contamination and abrasion of the contact lens and cornea. Particularly, in the case of a user with limited dexterity or long finger nails the risk of abrasion is significant. The need for a safe removal and insertion device is even more critical when the "user" of the device is not the contact lens wearer, but rather is a second party. In a medical emergency situation where there is possible injury to the eye, it is imperative that medical personel be able to quickly and safely remove the contact lens from the injured eye. Also, insertion of contact lens by a second party, i.e. hospital personel, is preferred where the wearer has limited dexterity or where therapeutic lens are prescribed for a patient.

The prior art devices do provide manipulating means which distance the fingertip and finger nail from possible contact with the eye; however, the further the user's finger is removed from the contact lens the less control the user has in applying or removing the lens. Thus, a device has been needed which insulates the eye and contact lens from abrasion or contamination, yet is simple enough to be convenient and provides adequate control in the application and removal of the lens.

The present invention solves the above discussed problems and is composed of a soft and sterile material which is designed to maintain the shape of the contact lens for insertion into the eye. The device also provides for an adhesive means, thus providing maximum control for the insertion and removal of the contact lens while maintaining sufficient distance between the surface of the eye and the fingertip.

SUMMARY OF THE INVENTION

It is the object of the present invention to provide a device for the handling of contact lenses which is convenient to use, simple in construction and safe.

Another object of the present invention is to provide a device which adequately maintains the shape of soft contact lenses but readily releases the contact lens when applied to the surface of the eye.

A further object of the present invention is to provide a device for the removal of contact lenses, both hard and soft, with reduced risk of abrasion or contamination of the lens or eye.

A still further object of the invention is to provide a device for handling contact lenses during their cleaning or sterilization.

These objects, and others which are apparent to persons skilled in the art reading this specification, are achieved by the device of the present invention, one embodiment of which may include a disc having a generally circular central aperture, said disc being coated on at least one side with a bio-compatible adhesive. The disc of the instant invention may be of any geometric shape including, but not limited to, rectangular, square, triangular, or circular, depending on manufacturing expedience. With respect to manufacturing expedience, the disc of the instant invention is most preferably made by multiply perforating a sheet of the disc material to form the central circular apertures and then cutting the sheet into any one of the above mentioned individual disc shapes. For application, cleaning, and sterilization of contact lenses, a bio-compatible adhesive must be applied to at least one side of the disc in order to provide an attachment to the fingertip, cleaning or sterilizing apparatus surfaces. For removal of contact lenses from the eye, at least two surfaces of the disc must be coated with adhesive in order to provide attachment to the fingertip and insure sufficient adhesion to the contact lens to overcome the surface tension holding the contact lens to the eye. A further embodiment of the instant invention provides for a disposable foam disc with the adhesive layer being an intergal part thereof. An alternative embodiment provides for a reusable disc with separate replacable adhesive coated bands. The latter embodiment allows the user to apply adhesive bands to either one or both sides of the disc for application or removal respectively. After use, the adhesive bands can be discarded and the disc sterilized for future use. The discs of the present invention can be simultaneously and conveniently sterilized by inclusion in the "heat or cold" disinfection processes commonly used for contact lenses.

The dimensions of the disc and central aperture are determined by evaluation of fingertip and contact lens size with preferred dimensions of the disc being 7 to 15 mm in diameter or width and 2 to 10 mm in thickness. The preferred size for the central aperture is 5 to 10 mm in diameter.

DETAILED DESCRIPTION

Figure 2:
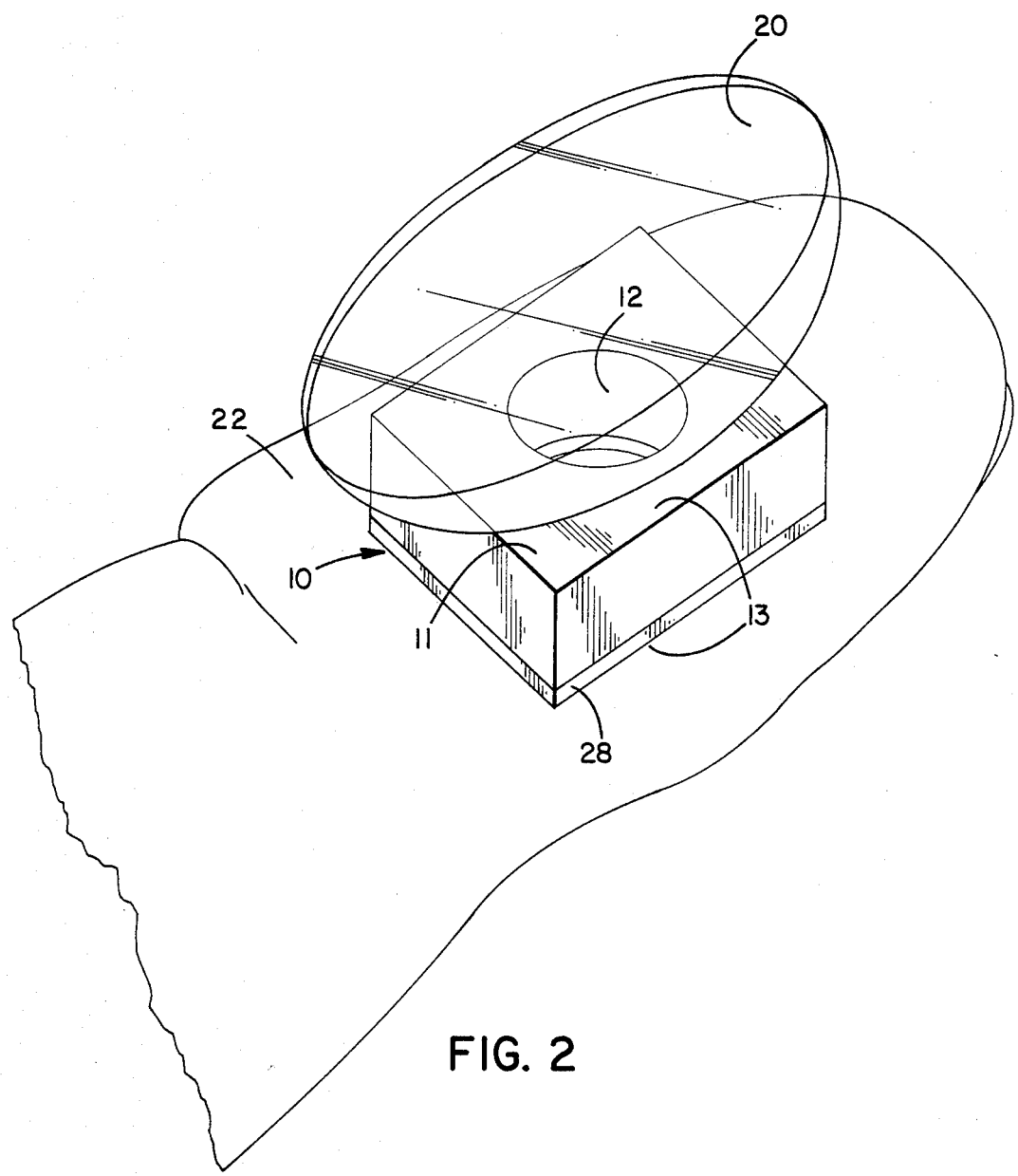
FIG. 2 shows an embodiment of the device of the present invention supporting the contact lens on the fingertip of the user wherein the disc is square in shape.

As previously stated, the present invention relates to a device for the handling of contact lenses, including, application, removal, cleaning, and sterilization. A preferred embodiment of the device according to the present invention is shown in FIG. 2 and generally designated by reference numeral 10. In this discussion of the instant invention, reference numerals may apply to identical elements in different embodiments.

The device 10 includes three sections, a square disc 11, a central circular aperture 12 and adhesive layers 13 which may be disposed on either one or both sides of disc 11. Bottom adhesive layer 28 is shown in FIG. 2 causing disc 11 to adhere to finger 22. As can be seen with reference to FIG. 2, the outer dimensions of disc 11 are generally less than that of the width of the fingertip 22 and the diameter of aperture 12 is large enough to support contact lens 20 in a convex shape but small enough to maintain the mechanical strength of the entire disc 11. For insertion of contact lenses, the adhesive layer 28 is applied only to the fingertip side of disc 11.

Figure 3:
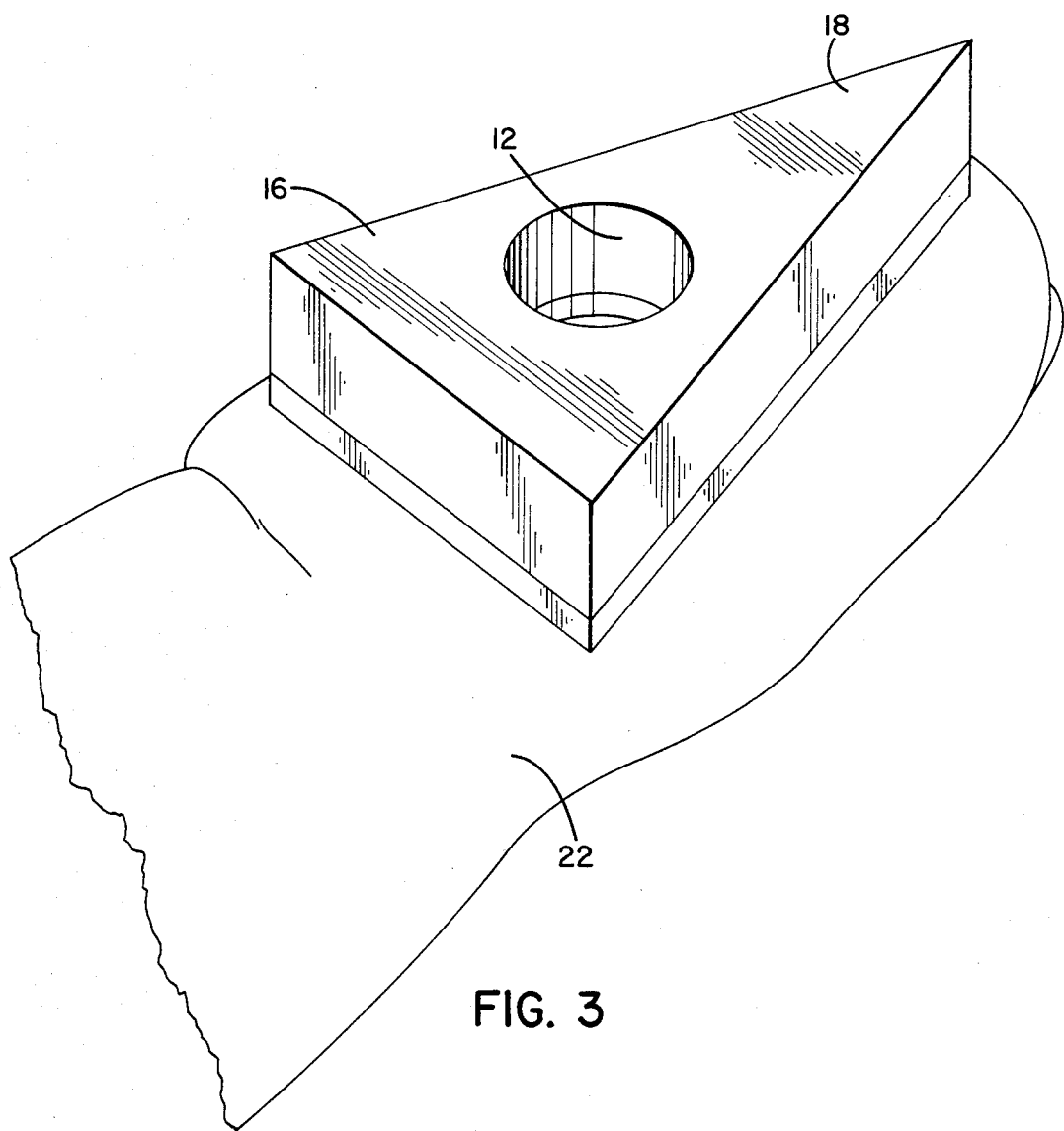
FIG. 3 shows an additional embodiment of the present invention as a triangular disc placed on the fingertip.

The triangular shaped disc element 16 of the device shown in FIG. 3 functions in the same manner as square disc 11 of FIG. 2, but has the additional advantage of having apex 18 of the triangular disc element 16 functioning as a distinctive mark for the orientation of astigmatic contact lenses prior to insertion into the eye. Moreover, the triangular shape approximates the narrowing of the fingertip of the user. Disc element 16 follows the structure of square disc 11, in having a central circular aperture 12 extending therethrough.

Figure 1:
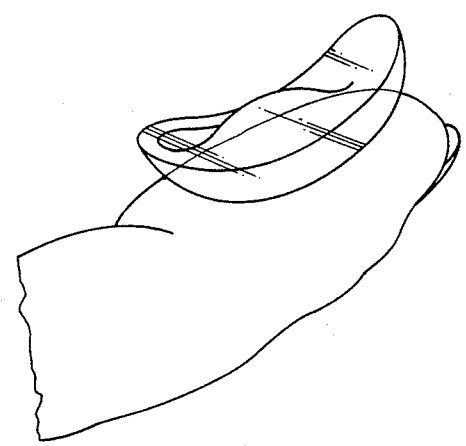
FIG. 1 shows a soft contact lens in a collapsed state on the fingertip of the user without the device of the present invention.
Figure 4:
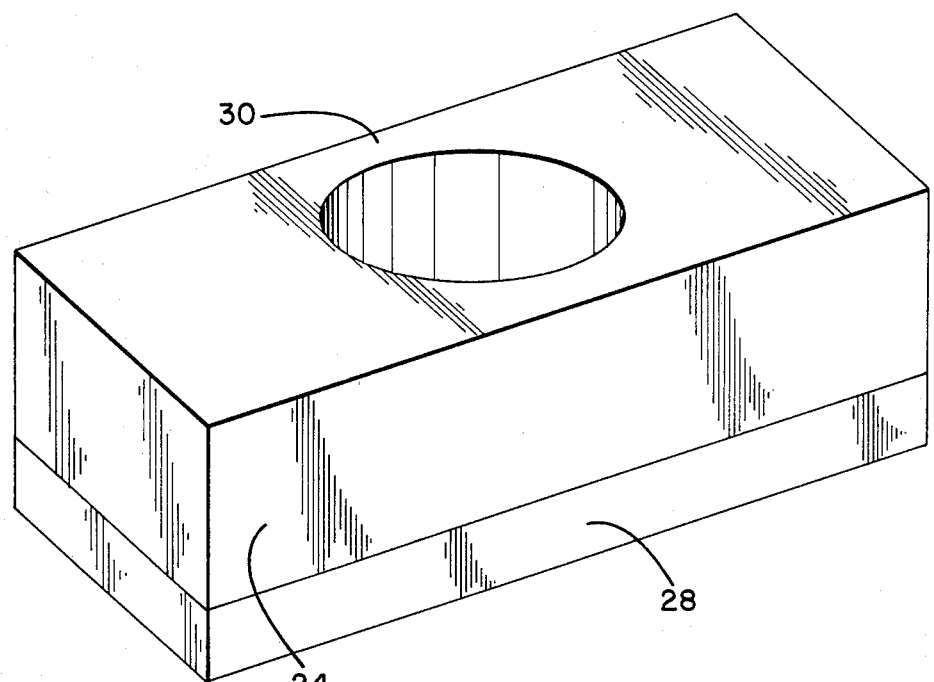
FIG. 4 shows a third embodiment of the present invention as a rectangular disc.

The rectangular disc 24 of FIG. 4 functions in the same manner as square disc 11 of FIG. 2, but has the advantage of increased surface area for adhesion to the fingertip. Additionally, in a preferred orientation, the longer side 30 of the rectangular shaped disc is placed longitudinally on the fingertip and corresponds well to the oval shape of the eye when the fingertip is positioned horizontally opposite the eye. Disc 24 is also provided with bottom adhesive layer 28.

Figure 5:
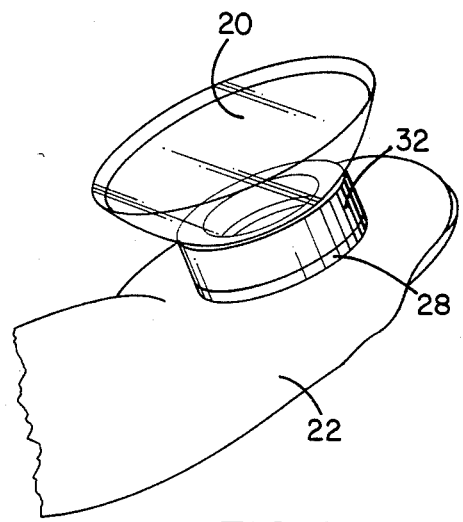
FIG. 5 shows a fourth embodiment of the present invention as a circular disc supporting a contact lens on the fingertip of the user.

FIG. 5 shows the circular embodiment of the present invention providing a circular disc 32 for the support of contact lens 20. Adhesive layer 28 is attached to the bottom of disc 32 and adheres said disc to finger 22 of the user. Disc 32 functions in the same manner as square disc 11, described above.

Figure 6:
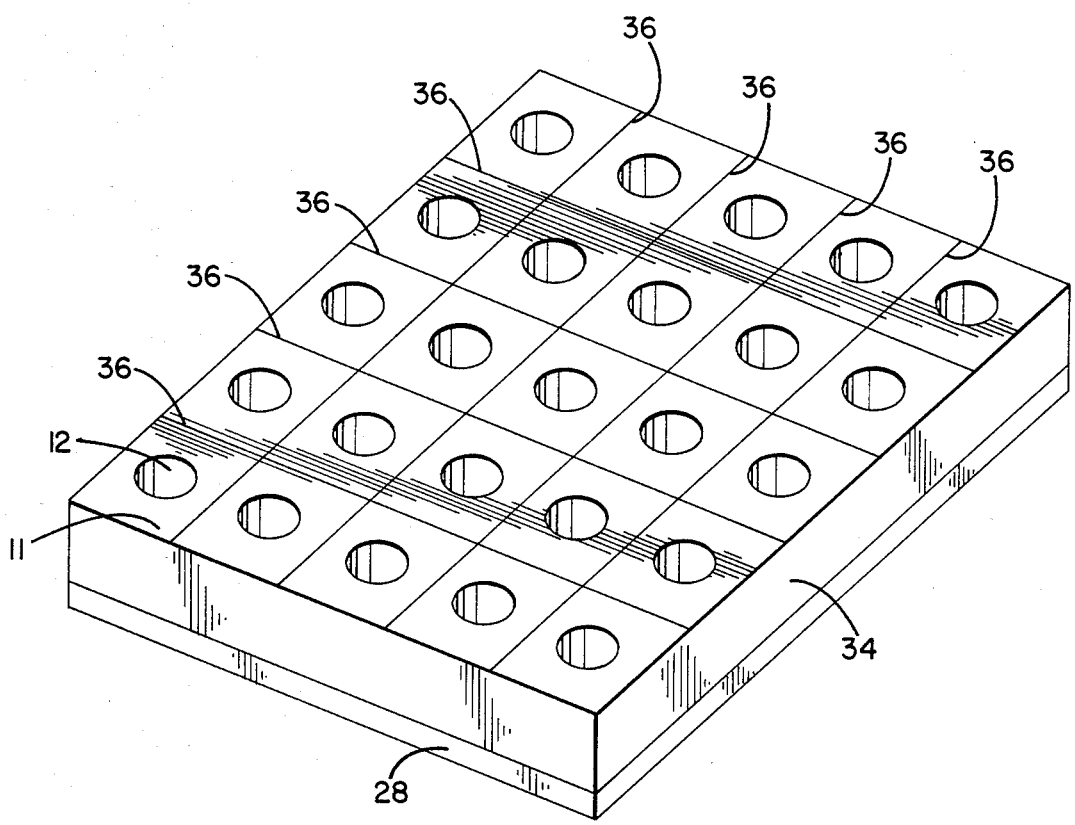
FIG. 6 shows a plurality of square discs in sheet form as an illustration of a possible manufacturing expedient.

The production of the present invention can be accomplished in a variety of ways, one of which is illustrated in FIG. 6. A sheet 34 of the disc material can be multiply perforated to form the central circular apertures 12 and then separated into individual discs 11 by cutting sheet 34 in the appropriate manner along cutting lines 36. Although FIG. 6 shows square discs, other geometric shapes may be obtained by using the appropriate cutting means.

Figure 7:
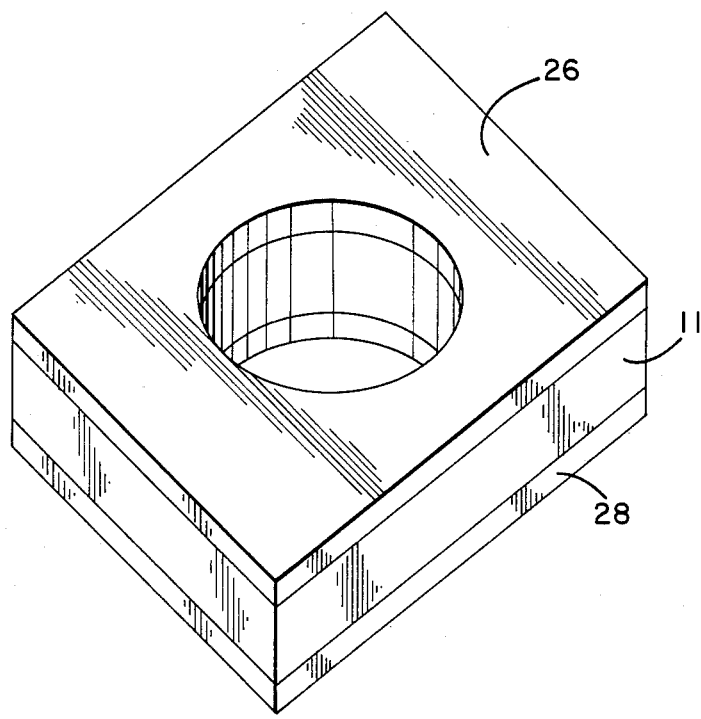
FIG. 7 shows the disc of the present invention coated on both sides with removable adhesive bands.

Adhesive layer 28 may be applied either before or after separation into separate devices. Preferably, the adhesive would be applied prior to separation of the individual devices. The adhesive may also be applied as a separate sheet which can be removed from the disc when the disc is to be reusable. This is illustrated in FIG. 7 where disc 11 is shown having top adhesive layer 26 and bottom layer 28 sandwiching disc 11 therebetween. The top adhesive layer 26 is optional and designed to assist in removal of the lens 20 from the eye of a wearer. Of course, top adhesive layer 26 may also be used on other embodiments of this invention although not shown in FIGS. 2, 3, 4, 5, and 6.

With respect to the composition of the present invention the structural materials and adhesive must be biocompatible and have the physical properties of being soft, compressible and pliable to facilitate control over the contact lens and reduce the risk of trauma to the eye in the event that it inadvertently touches the eye. Such materials may be a solid or a foam with the latter being open or closed cell foam. If open cell foam is used, a top film may be employed to eliminate any problems associated with the porosity of the open cell foam. The adhesive must be selected so as to provide adequate adhesion to the fingertip without contaminating the contact lens, in the case of removal of contact lens, or leaving residue on the fingertip. In addition to being bio-compatible, any materials used in the instant device must be chemically inert and not subject to degradation or alteration over a reasonable period of time.

The device will be manufactured and packaged in such a way as to insure that they are delivered to the user in a sterile condition. The devices may be packaged individually or in groups. Where the device is of the reusable type the discs and adhesive layers may be packaged separately. The adhesive bands are disposable and the disc layer is compatible with conventional disinfection techniques.

Where the device of the present invention is used to insert contact lenses into the eye, the user applies the device to the tip of the finger with the adhesive layer in contact therewith and then places the contact lens on the outer circumference of the aperture so that the lens is supported in its convex shape. The uses then applies the contact lens to the surface of the eye with release from the disc to the eye resulting when the surface area contact with the eye is greater than that of the contact of the lens with the disc.

When the present device is used to remove contact lenses, an adhesive layer is present on both sides of the disc with one side attached to the fingertip and the other side of the disc used to adhere to the contact lens and extract it from the eye. Once extracted the contact lens can be removed from the disc by use of the other hand.

When the device of the present invention is used in the cleaning or disinfection process the lens is simply placed on the disc and the disc is immersed in the cleaning or disinfection solution.

It will be recognized by those skilled in the art that the device of the present invention embodies a convenient, simple, and safe device for the insertion, removal and general handling of contact lenses. It will also be recognized that the various modifications may be made to the preferred embodiments without departing from the scope of the invention.

I claim:

1. A contact lens applicator, comprising:
   a base member having an upper surface and a lower surface, formed of a soft, biocompatible material;
   a generally circular aperture extending through the base member for supporting a contact lens, said aperture being dimensioned so that the upper surface supports the contact lens without collapse of the lens while maintaining sufficient mechanical strength for said base member;
   adhesive means for contacting the lower surface of said base member with a finger of a person applying the contact lens to an eye and securing the base member to the finger so that said lower surface is between said upper surface and the area of the finger contacted along a line generally perpendicular to the area of the finger contacted, said adhesive means being biocompatible.

2. The applicator of claim 1, wherein the shape of said base member is square.

3. The applicator of claim 1, wherein the shape of said base member is triangular.

4. The applicator of claim 1, wherein the shape of said base member is rectangular.

5. The applicator of claim 1, wherein the shape of said base member is circular.

6. The applicator of claim 1, wherein said base member is composed of a bio-compatible foam.

7. The applicator of claim 1, wherein said base member is composed of closed cell foam.

8. The applicator of claim 1, wherein said base member and said adhesive means are separable, with said base member being reusable after sterilization.

9. The applicator of claim 1, wherein the base member is composed of plastic.

10. The applicator of claim 1, wherein said base member is composed of rubber.

11. The applicator of claim 1, wherein said base member is composed of cloth.

12. The applicator of claim 1, wherein said adhesive means is an adhesive coating layer laminated to said lower surface.

13. The applicator of claim 12, wherein both said base member and said adhesive coating layer are intended for disposal after use.

14. The applicator of claim 12, wherein an adhesive coating layer also is laminated to the upper surface of said base member.

* * * * *